(12) United States Patent
Nelson et al.

(10) Patent No.: US 6,562,215 B1
(45) Date of Patent: May 13, 2003

(54) PLANAR EXHAUST SENSOR ELEMENT WITH ENHANCED GEOMETRY

(75) Inventors: Charles Scott Nelson, Clio, MI (US); David K. Chen, Rochester Hills, MI (US); Lora B. Younkman, Grand Blanc, MI (US); Raymond L. Bloink, Swartz Creek, MI (US); Kaius K. Polikarpus, Grand Blanc, MI (US); Walter T. Symons, Grand Blanc, MI (US)

(73) Assignee: Delphi Technologies, Inc., Troy, MI (US)

( * ) Notice: Subject to any disclaimer, the term of this patent is extended or adjusted under 35 U.S.C. 154(b) by 1 day.

(21) Appl. No.: 09/633,420

(22) Filed: Aug. 7, 2000

(51) Int. Cl.[7] .............................................. G01N 27/407
(52) U.S. Cl. ........................ 204/784; 204/424; 204/426
(58) Field of Search ................. 204/421–429; 205/783–785

(56) References Cited

U.S. PATENT DOCUMENTS

| | | | | |
|---|---|---|---|---|
| 4,076,608 A | * | 2/1978 | Fujishiro et al. |
| 4,547,281 A | * | 10/1985 | Wang et al. |
| 4,597,850 A | * | 7/1986 | Takahashi et al. |
| 4,657,659 A | * | 4/1987 | Mase et al. |
| 5,830,339 A | * | 11/1998 | Watanabe et al. |

* cited by examiner

Primary Examiner—T. Tung
(74) Attorney, Agent, or Firm—Vincent A. Cichosz

(57) ABSTRACT

Disclosed herein is a planar exhaust gas sensor for sensing the partial pressure of a gas in an exhaust. The sensing element has a modified, non-rectangular overall geometry. A terminal end of the element, onto which external sensor circuits can be attached, has a larger width than a sensor end of the element, in which is located the sensing cell. The reduced size of the sensor end of the element relative allows for more rapid attainment of operating temperature and lower energy consumption.

16 Claims, 5 Drawing Sheets

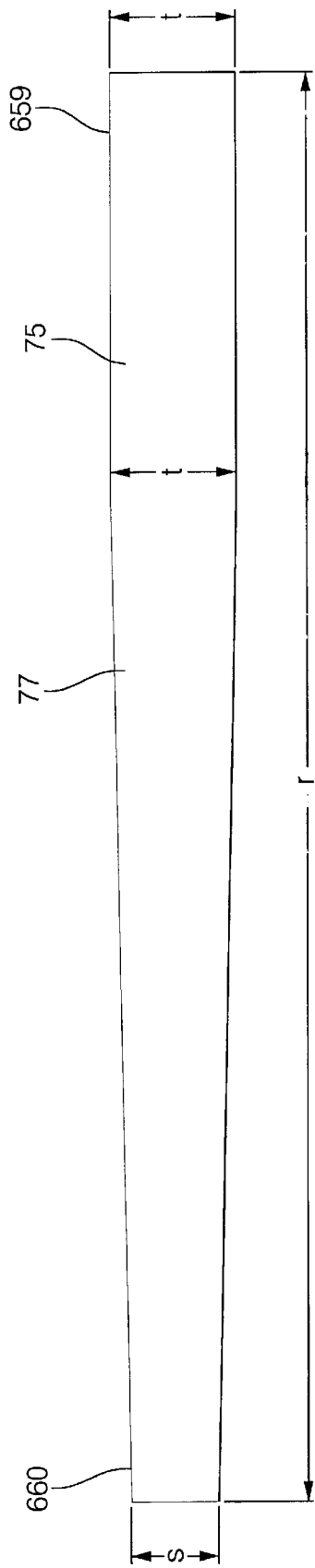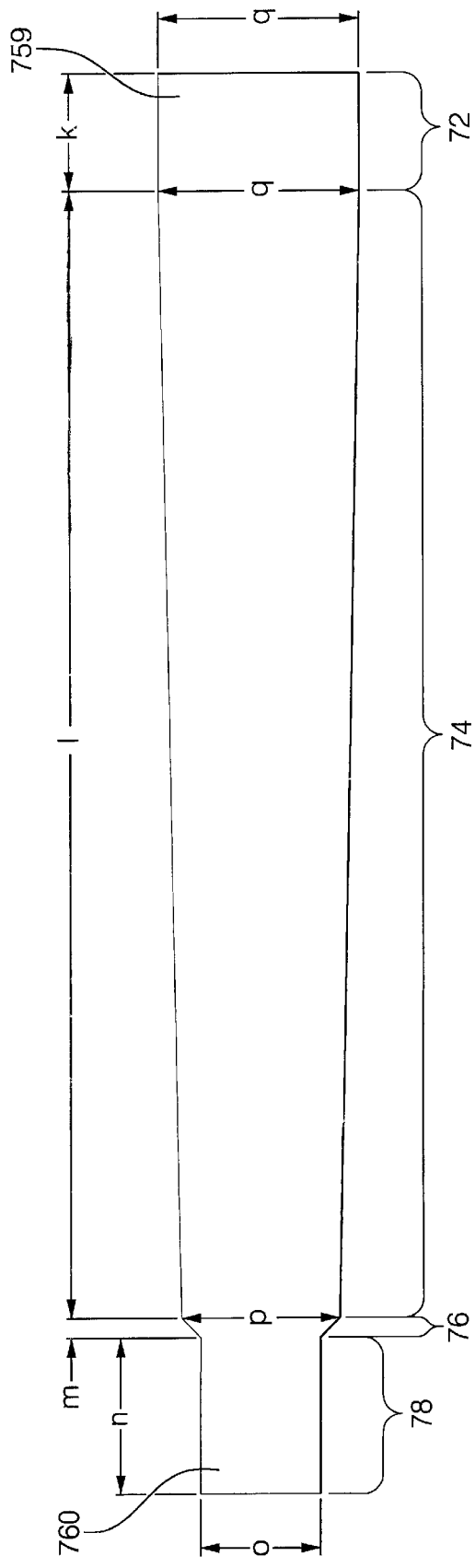
FIG. 6
FIG. 7

PLANAR EXHAUST SENSOR ELEMENT WITH ENHANCED GEOMETRY

BACKGROUND OF THE INVENTION

This invention relates generally to exhaust gas sensors, and specifically to oxygen sensors.

Oxygen sensors are used in a variety of applications that require qualitative and quantitative analysis of gases. In automotive applications, the direct relationship between oxygen concentration in the exhaust gas and air to fuel ratio of the fuel mixture supplied to the engine allows the oxygen sensor to provide oxygen concentration measurements for determination of optimum combustion conditions, maximization of fuel economy, and the management of exhaust emissions.

A conventional stoichiometric oxygen sensor typically consists of an ionically conductive solid electrolyte material, a porous electrode on the sensor's exterior exposed to the exhaust gases with a porous protective overcoat, and a porous electrode on the sensor's interior surface exposed to a known oxygen partial pressure. Sensors typically used in automotive applications use a yttria stabilized zirconia based electrochemical galvanic cell with porous platinum electrodes, operating in potentiometric mode, to detect the relative amounts of oxygen present in an automobile engine's exhaust. When opposite surfaces of this galvanic cell are exposed to different oxygen partial pressures, an electromotive force is developed between the electrodes on the opposite surfaces of the zirconia wall, according to the Nernst equation:

$$E = \left(\frac{RT}{4F}\right)\ln\left(\frac{P_{O_2}^{ref}}{P_{O_2}}\right)$$

where:

$E$ = electromotive force $R$ = universal gas constant $F$ = Faraday constant $T$ = absolute temperature of the gas $P_{O_2}^{ref}$ = oxygen partial pressure of the reference gas $P_{O_2}$ = oxygen partial pressure of the exhaust gas Due to the large difference in oxygen partial pressure between fuel rich and fuel lean exhaust conditions, the electromotive force changes sharply at the stoichiometric point, giving rise to the characteristic switching behavior of these sensors. Consequently, these potentiometric oxygen sensors indicate qualitatively whether the engine is operating fuel rich or fuel lean, without quantifying the actual air to fuel ratio of the exhaust mixture.

Increased demand for improved fuel economy and emissions control has necessitated the development of oxygen sensors capable of quantifying the exhaust oxygen partial pressure over a wide range of air fuel mixtures in both fuel-rich and fuel-lean conditions. As is taught by U.S. Pat. No. 4,863,584 to Kojima et al., U.S. Pat. No. 4,839,018 to Yamada et al., U.S. Pat. No. 4,570,479 to Sakurai et al., and U.S. Pat. No. 4,272,329 to Hetrick et al., an oxygen sensor which operates in a diffusion limited current mode produces a proportional output which provides a sufficient resolution to determine the air-to-fuel ratio under fuel-rich or fuel-lean conditions. Generally, diffusion limited current oxygen sensors have a pumping cell and a reference cell with a known internal or external oxygen partial pressure reference. A constant electromotive force, typically corresponding to the stoichiometric electromotive force, is maintained across the reference cell by pumping oxygen through the pumping cell. The magnitude and polarity of the resulting diffusion limited current is indicative of the exhaust oxygen partial pressure and, therefore, is a measure of air-to-fuel ratio.

As is taught by U.S. Pat. No. 4,450,065, wide range oxygen sensors commonly employ an aperture with a cross-sectional area to length ratio sufficiently small to limit exhaust gas diffusion. In this sensor, a gap between the pumping and reference cells forms such an aperture and limits diffusion of exhaust gas to a common environment between the two cells. This common environment, or diffusion chamber is required in an aperture construction for adequate mixing of the diffused exhaust gas; however, it tends to slow the frequency response of the sensor operation. Additionally, although the two electrodes adjacent to the diffusion chamber can be shorted together to eliminate one lead, four separate electrodes are required in this construction.

Commonly assigned U.S. Pat. No. 5,360,528 to Oh et al., teaches a wide range oxygen sensor having improved mass production capabilities. This wide range oxygen sensor employs a porous layer, formed by plasma spray deposition, to limit oxygen diffusion in lieu of the diffusion limiting aperture. This wide range oxygen sensor has a planar structure with a single solid electrolyte layer shared by electrochemical storage, pumping, and reference cells. The electrochemical pumping cell has a diffusion layer formed from a porous ceramic to permit diffusion of oxygen molecules through this layer.

Planar exhaust sensor elements comprising a plurality of rectangular layers are known to reach operating temperature more rapidly than conical sensors. Planar exhaust sensors have been reduced in size in order to reach operating temperature even more rapidly, but size reduction requires increased complexity for the electrical interconnection to the sensor element. Additionally, leads to the heater element disposed within the sensor element must be reduced in size as well, which leads to greater electrical resistance in the heater element leads, and a commensurate loss of energy.

Also, linear oxygen sensors can have two to five more leads than conventional stoichiometric sensor elements. The extra leads require connections that must be secured to the exterior of the connection end of the sensor element. As sensor size is decreased to gain a performance advantage, the area for connecting the extra leads to external circuits is reduced, and ensuring secure connections becomes more difficult.

What is needed in the art is a sensor element that reaches operating temperature more rapidly than conventional sensors, without increasing energy losses, and without significantly reducing the sensor area in which leads are connected to external circuits.

BRIEF SUMMARY OF THE INVENTION

Herein is described an electrochemical cell, an exhaust gas sensor element, and a method for using the sensor element. The electrochemical cell comprises: a substrate layer with a terminal end and a sensor end, wherein the sensor end is narrower than the terminal end; an electrolyte disposed in the sensor end; an outer electrode disposed in intimate contact with one side of the electrolyte; and, an inner electrode disposed in intimate contact with another side of the electrolyte, opposite the outer electrode.

The sensor element comprises: a plurality of layers comprising a sensor end and a terminal end opposite said sensor end, wherein said layers are disposed in physical contact in a stack, and the width of said sensor end is smaller than the terminal end width. An electrochemical cell is disposed in said sensor end of said layers; and a plurality of electrode leads disposed in electrical contact with the cell, extending from the cell to the terminal end.

The method of using this sensor element comprises: exposing the sensor element to the exhaust gas; diffusing molecular oxygen in the exhaust gas through a gas diffuser to the cell; ionizing the molecular oxygen at an inner electrode of the electrochemical cell; applying a potential between the inner electrode and an outer electrode of the electrochemical cell; and measuring a current produced by the potential.

The above-described and other features and advantages of the present invention will be appreciated and understood by those skilled in the art from the following detailed description, drawings, and appended claims.

BRIEF DESCRIPTION OF THE DRAWINGS

The apparatus and method will now be described by way of example, with reference to the accompanying drawings, which are meant to be exemplary, not limiting.

FIG. 6 is a plan view of another embodiment of a layer of a planar exhaust sensor element with a tapered region and a rectangular region.

FIG. 7 is a plan view of yet another embodiment of a layer of a planar exhaust sensor element with two tapering regions and two rectangular regions.

DETAILED DESCRIPTION OF THE INVENTION

A gas sensor is described herein, wherein a planar sensor element has an enhanced geometry to facilitate reaching operating temperature rapidly upon startup. Whereas conventional planar sensor elements have used rectangular layers, the exhaust gas sensor described herein uses modified, non-rectangular sensor geometries. It is hereby understood that although the apparatus and method are described in relation to making a linear oxygen sensor, the sensor could be a stoichiometric sensor, a nitrogen oxide sensor, a hydrogen sensor, a hydrocarbon sensor, or the like.

Figure 1:
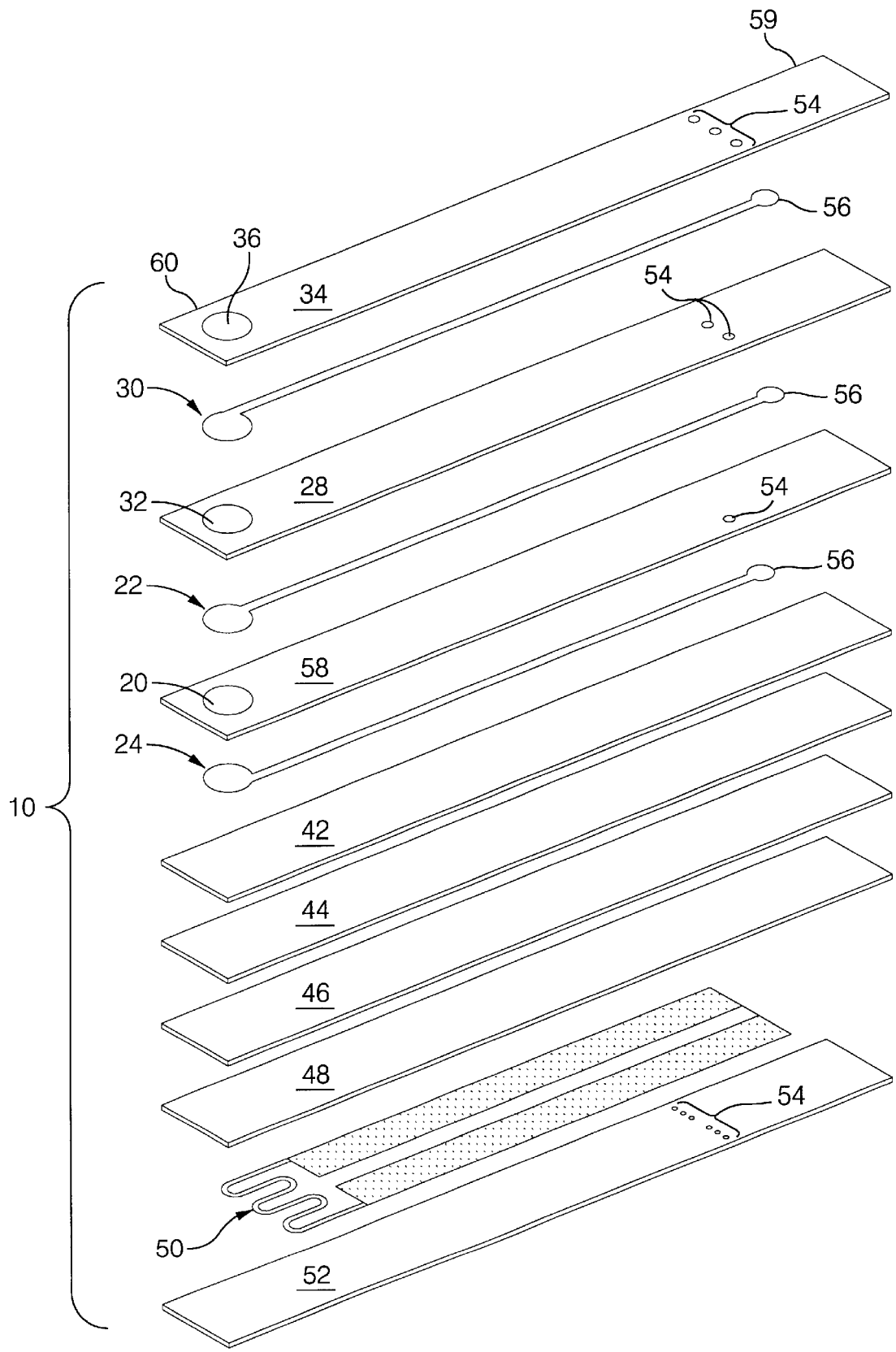
FIG. 1 is an exploded view of one embodiment of a planar exhaust sensor element.

FIG. 1 shows one embodiment of the arrangement of the different layers of a sensor element, wherein the sensor element 10 comprises a first electrolyte 20 disposed in a dielectric layer 58, with an inner electrode 22 and a reference electrode 24 disposed on opposite sides of the first electrolyte 20, a second electrolyte 32 disposed in electrical communication with the inner electrode 22 and disposed in a dielectric layer 28; an outer electrode 30 disposed on the side of the second electrolyte 32 opposite said inner electrode 22; and a dielectric layer 34 disposed against said dielectric layer 28 opposite said dielectric layer 58. The element 10 further comprises internal support layer 42 disposed against said dielectric layer 58; a heater 50 disposed between said support layer 48 and a protective outer layer 52; an optional protective material 36 disposed in physical contact with the outer electrode 30 and in said dielectric layer 34; vias 54 defined by said dielectric layers 34, 28, 58, and outer layer 52; leads 56 in electrical communication with each of the electrodes 30, 22, 24; a terminal end 59; and a sensor end 60.

The electrodes 30, 22, 24 and electrolyte 32, 20 form electrochemical cells. The outer electrode 30, second electrolyte 32, and inner electrode 22 form a pumping cell, while the inner electrode 22, first electrolyte 20, and reference electrode 24 form a reference cell. Oxygen in the exhaust enters the pumping cell through the protective material 36, and diffuses through the outer electrode 30 and second electrolyte 32 to the inner electrode 22, where it is ionized and pumped back out of the cell. Generally a reference cell is used in combination with the pumping cell, but the pumping cell can be used as the only electrochemical cell in the sensor in lean-only applications. The reference cell is used to compare the partial pressure of oxygen at the inner electrode 22 with a known oxygen partial pressure at the reference electrode 24 in order to determine the potential that should be applied to the pumping cell. The measured current in the pumping cell will be directly proportional to the partial pressure of oxygen in the exhaust gas.

The solid electrolyte layer 20 can be any material that is capable of permitting the electrochemical transfer of oxygen ions while inhibiting the physical passage of exhaust gases, has an ionic/total conductivity ratio of approximately unity, and that is compatible with the environment in which the sensor will be utilized (e.g., up to about 1,000° C). Possible solid electrolyte materials include conventional materials, e.g. metal oxides including zirconia and the like, such as yttria stabilized zirconia, calcia stabilized zirconia, and magnesia stabilized zirconia, among other materials, and combinations comprising at least one of the foregoing. Typically, the solid electrolyte has a thickness of up to about 500 microns, with a thickness of approximately 25 microns to about 500 microns preferred, and a thickness of about 50 to about 200 microns especially preferred.

As with the first electrolyte 20, the second electrolyte 32 makes use of an applied electrical potential to influence the movement of oxygen. The second electrolyte 32 can be porous or solid. If porous, the second electrolyte 32 should be capable of permitting the physical migration of exhaust gas and the electrochemical movement of oxygen ions, and should be compatible with the environment in which the sensor is utilized. Typically, a porous second electrolyte 32 has a porosity of up to about 20%, with a median pore size of up to about 0.5 microns, or, alternatively, comprises a solid electrolyte having one or more holes, slits, or apertures therein, so as to enable the physical passage of exhaust gases. Commonly assigned U.S. Pat. No. 5,762,737 to Bloink et al., which is hereby incorporated in its entirety by reference, further describes porous electrolytes useful herein. Possible porous electrolyte materials include those listed above for the first electrolyte 20.

The electrolytes 32, 20 can be formed via many conventional processes including, but not limited to, die pressing, roll compaction, stenciling, screen printing, and the like. For improved process compatibility, it is preferred to utilize a tape process using known ceramic tape casting methods.

The various electrodes 22, 24, 30 disposed in contact with the first electrolyte 20 and the second electrolyte 32 can comprise any catalyst capable of ionizing oxygen, including, but not limited to, noble metal catalysts such as platinum, palladium, gold, rhodium, and the like, other metals and metal oxides, and other conventional catalysts including mixtures and alloys comprising at least one of these materials. The electrodes preferably have a porosity sufficient to permit the diffusion of oxygen molecules without substantially restricting such gas diffusion. Typically, the porosity is greater than the porosity of the second electrolyte 32, and the size and geometry of the electrodes are adequate to provide current output sufficient to enable reasonable signal resolution over a wide range of air/fuel ratios, while preventing leakage between electrolytes. Generally, a thickness of about 1.0 to about 25 microns can be employed, with a thickness of about 5 to about 20 microns preferred, and about 10 to about 18 more preferred. The geometry of the electrodes is preferably substantially similar to the geometry of the electrolyte, with at least a slightly larger overall size than the electrolyte preferred to ensure that the electrodes cover the electrolyte, thereby preventing leakage between electrolytes and allowing sufficient print registration tolerance.

The electrodes can be formed using conventional techniques such as sputtering, chemical vapor deposition, screen printing, and stenciling, among others, with screen printing the electrodes onto appropriate tapes preferred due to simplicity, economy, and compatibility with the subsequent co-fired process. For example, reference electrode 24 can be screen printed onto layer 42 or onto the first electrolyte 20, inner electrode 22 can be screen printed onto first electrolyte 20 or second electrolyte 32, and outer electrode 30 can be screen printed onto the second electrolyte 32 or layer 34, over the protective material 36, if present. Electrode leads 56 and vias 54 in the alumina layers are typically formed simultaneously with the electrodes.

Although the porosity of the reference electrode 24 is typically sufficient to hold an adequate quantity of oxygen to act as a reference, a space for storing reference oxygen (not shown) can be provided between the reference electrode 24 and the adjoining layer 42. This space can be formed by depositing a carbon base material, i.e., a fugitive material, between the reference electrode 24 and the layer 42 such that upon processing the carbon burns out, leaving a space.

In order to prevent poisoning of the outer electrode 30, a gas diffuser, e.g., protective material 36, can optionally be disposed in layer 34 or elsewhere where the exhaust gas accesses the inner electrode 22. In the embodiment shown in FIG. 1, the protective material 36 enables access of exhaust gas to inner electrode 22 through the outer electrode 30 and the second electrolyte 32, while inhibiting the passage of particulates and/or contaminants in the exhaust gas. Possible protective materials include those conventionally known in the art. Alternatively, if a protective material 36 is not employed in layer 34, another gas diffuser, e.g., aperture or the like, can be employed to enable exhaust gas access to inner electrode 22.

The electrolytes 20, 32 and the protective material 36 can be disposed as inserts in layers 28, 34, 58 or otherwise attached to the layers 28, 34, 58. Disposing the electrolytes 20, 32 and the optional protective material 36 as inserts eliminates the use of excess electrolyte and protective material, and reduces the size of the sensor by eliminating layers. Any shape can be used for the second electrolyte 32, first electrolyte 20, and protective material 36, since the size and geometry of the various inserts, and therefore the corresponding openings, are dependent upon the desired size and geometry of the adjacent electrodes. It is preferred that the openings, inserts, and electrodes have a substantially similar geometry. Some possible insert geometries include elongated shapes, such as oval, rectangular, square, quadrilateral, polygon, or the like, as well as other shapes.

The layers 28, 34, 58 as well as the other substrate layers 42, 52, are dielectric materials which effectively protect various portions of the sensor, provide structural integrity, and separate various components. Layers 42 electrically isolate the heater circuit from the sensor circuits, while layers 34 and 52 physically cover the outer electrode 30 and lead 56, and heater circuit 50, respectively, to provide physical protection, against, for example, abrasion, and to electrically isolate these components from the packaging. Preferably, these layers 28, 34, 42, 52, 58, comprise material, such as alumina, having substantially equivalent coefficients of thermal expansion, shrinkage characteristics, and chemical compatibility, to at least minimize, if not eliminate, delamination and other processing problems.

The layers 28, 34, 42, 52, 58, can be up to about 200 microns or more thick, with a thickness of about 50 to about 200 microns preferred. As with the solid and porous electrolytes, these layers can be formed using ceramic tape casting methods or other methods such as plasma spray deposition techniques, screen printing, stenciling and others conventionally used in the art.

Disposed between two of the substrate layers 48, 52 is a heater 50, with a ground plane (not shown) optionally disposed between two other substrate layers. The heater 50 can be any conventional heater capable of maintaining sensor end 60 of the oxygen sensor at a sufficient temperature to facilitate the various electrochemical reactions therein. Typically the heater, which is platinum, palladium, alumina, or alloys or mixtures comprising at least one of the foregoing, or any other conventional heater, is generally screen printed onto a substrate to a thickness of about 5 to about 50 microns.

Leads 56 are disposed across various dielectric layers to electrically connect the external wiring of the sensor with electrodes 30, 22, 24. The leads 56 are typically formed on the same layer as the electrode to which they are in electrical communication, and extend from the electrode to the terminal end 59 of the element where they are in electrical communication with the corresponding via 54. The heater 50 also has leads that are in electrical communication with vias 54.

At the terminal end 59 of the element, the vias 54 are formed as holes filled with electrically conductive material in the appropriate layers 34, 28, 58, and 52. The vias 54 are typically filled during formation of the electrodes 30, 22, 24 and leads 56, and serve to provide a mechanism for electrically connecting the leads 56 and heater 50 to the exterior of the element. The vias 54 are in electrical communication with contact pads (not shown) which are formed on the exterior surface of the outside layers 34, 52. The contact pads provide a contact point for the external sensor circuit.

While it is desirable for the terminal end 59 of the element to be wide enough to allow for well distinguished contact pads for secure and precise attachment of an external electrical circuit to the element, it is not desirable for the sensor end 60 of the element to be wide, since additional current would thereby be required to heat the sensor end 60 of the element to operating temperatures.

Figure 2:
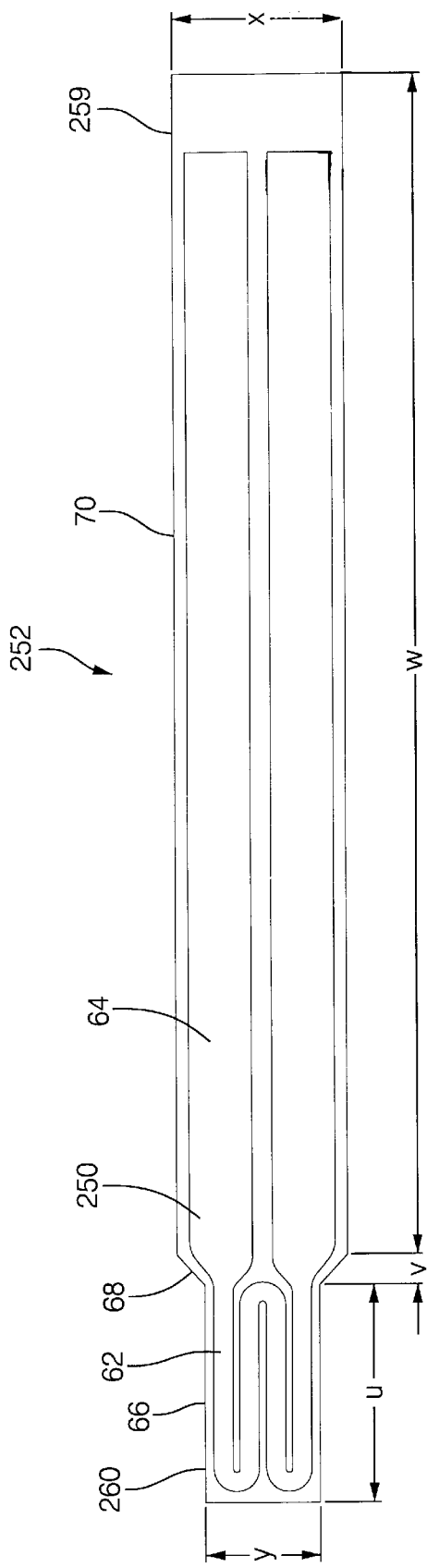
FIG. 2 is a plan view of one embodiment of a layer of a planar exhaust sensor element with a single tapering region between two rectangular regions.

FIG. 2 shows one embodiment of a single layer 252 of the sensor element with a modified, non-rectangular overall geometry. A heater 250 is disposed on the substrate layer 252, which has a terminal end 259 and a sensor end 260, as well as a wide portion 70 and a narrow portion 66, which preferably have a common central axis, between which is disposed a tapering portion 68. The wide portion 70 and narrow portion 66 are generally quadrilaterals, with a rectangular shape preferred, wherein the long sides of the rectangle of the wide portion 70 are parallel with the long sides of the rectangle of the narrow portion 66. FIG. 2 shows only a single layer of the element, and, although different geometries can be used for the separate layers of the sensor element, it is preferable that all of the layers have essentially the same geometry in any single embodiment so that when the various layers are combined to form the finished sensor, the overall geometry of the element is the same as the individual layers.

The heater 250 has a lead portion 64 and a heating portion 62. The lead portion 64 is formed so as to have low electrical resistance, which is accomplished by forming the lead portion 64 from materials with high conductivity while widening the leads over the surface of the layer 252 as much as possible without causing shorts. The heating portion 62, conversely, can be formed from material with lower conductivity and can be formed in a narrow strip to increase resistance in this portion of the heater circuit. Although the heater 250 can be configured in any manner that provides optimal heating of the sensor end 260 of the element, the heater 250 will preferably conform to the geometry of the support layer 252 on which it is disposed. That is, the heater is typically configured to occupy as much of the layer 252 as possible for any embodiment without causing shorts.

Preferably, substrate layer 252 has a shape that allows rapid and efficient heating of the sensor end 260 of the element. The ratio of the width of the narrow portion 66, "y", to the width of the wide portion 70, "x", in all embodiments, can be any ratio less than 1:1, and preferably is about 7:12 to about 11:12, with a ratio of about 2:3 to about 5:6 especially preferred. The ratio of the length of the narrow portion 66, "u", to the length of the wide portion 70, "w", can be any ratio less than about 1:2, and preferably is about 1:4 to about 1:7, with a ratio of about 2:11 especially preferred. The ratio of the length of the tapering portion 68 of the element "v" to the entire length of the element (u+v+w) can be any ratio, and preferably is less than about 1:25, with a ratio of about 1:50 especially preferred.

Figure 3:
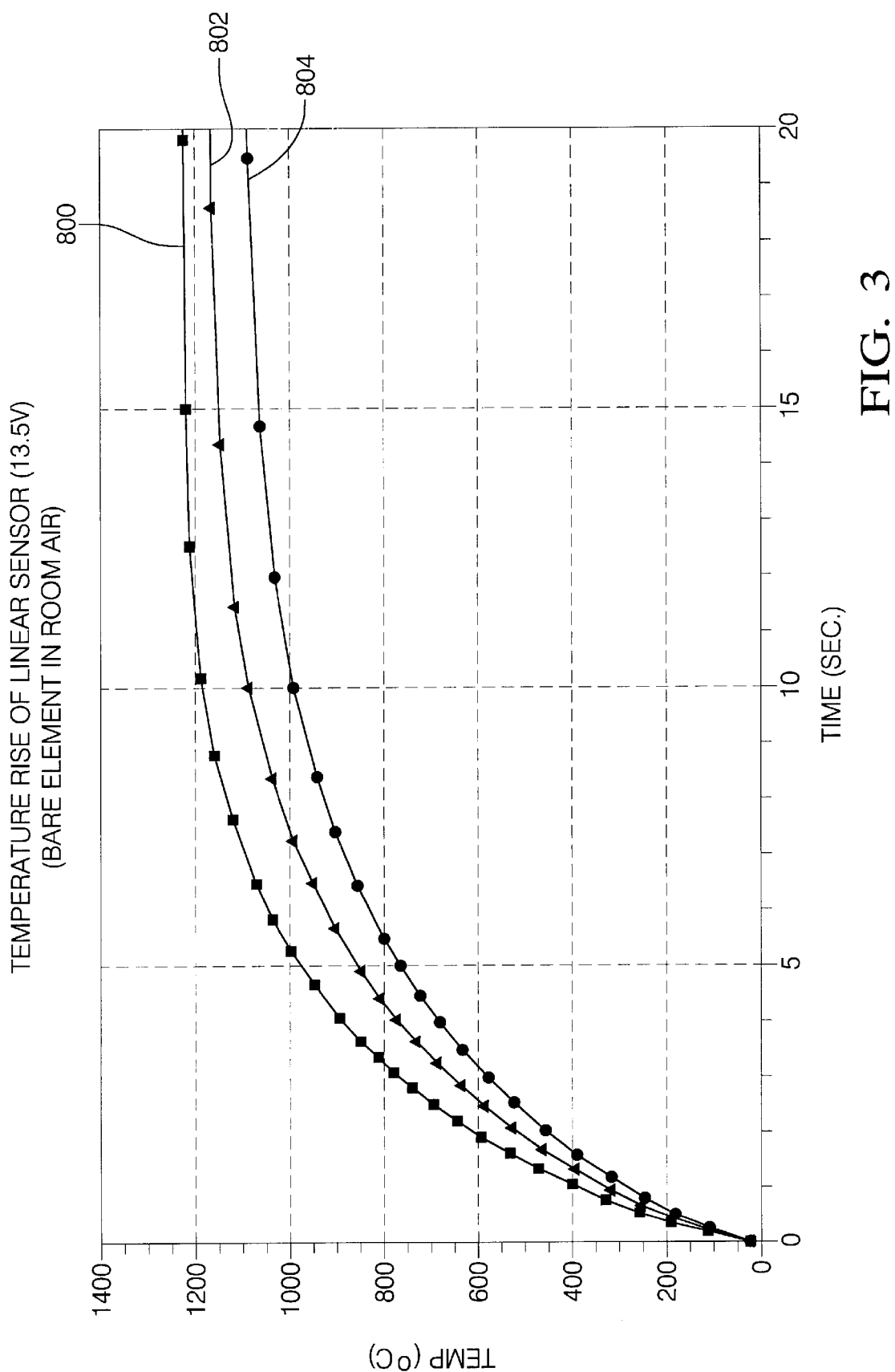
FIG. 3 is a graph showing the relative temperature rise of planar sensing elements having various geometries.

FIG. 3 shows a graph of the temperature after start-up of three sensor elements over time with an applied voltage of 13.5 volts. The conventional rectangular element (line 804) is heated more slowly than the elements with either a 5:6 (line 802) or 2:3 (line 800) narrow portion 66 width to wide portion 70 width ratio as described above and shown in FIG. 2. In both cases, the ratio of the length of the tapering portion 68 to the entire length of the element is about 1:50. The temperature of the element is measured at the sensing end. The temperature of the sensing end increases more rapidly for the modified geometry element because the cross-sectional area of the sensing end is smaller than for conventional rectangular elements.

Figure 4:
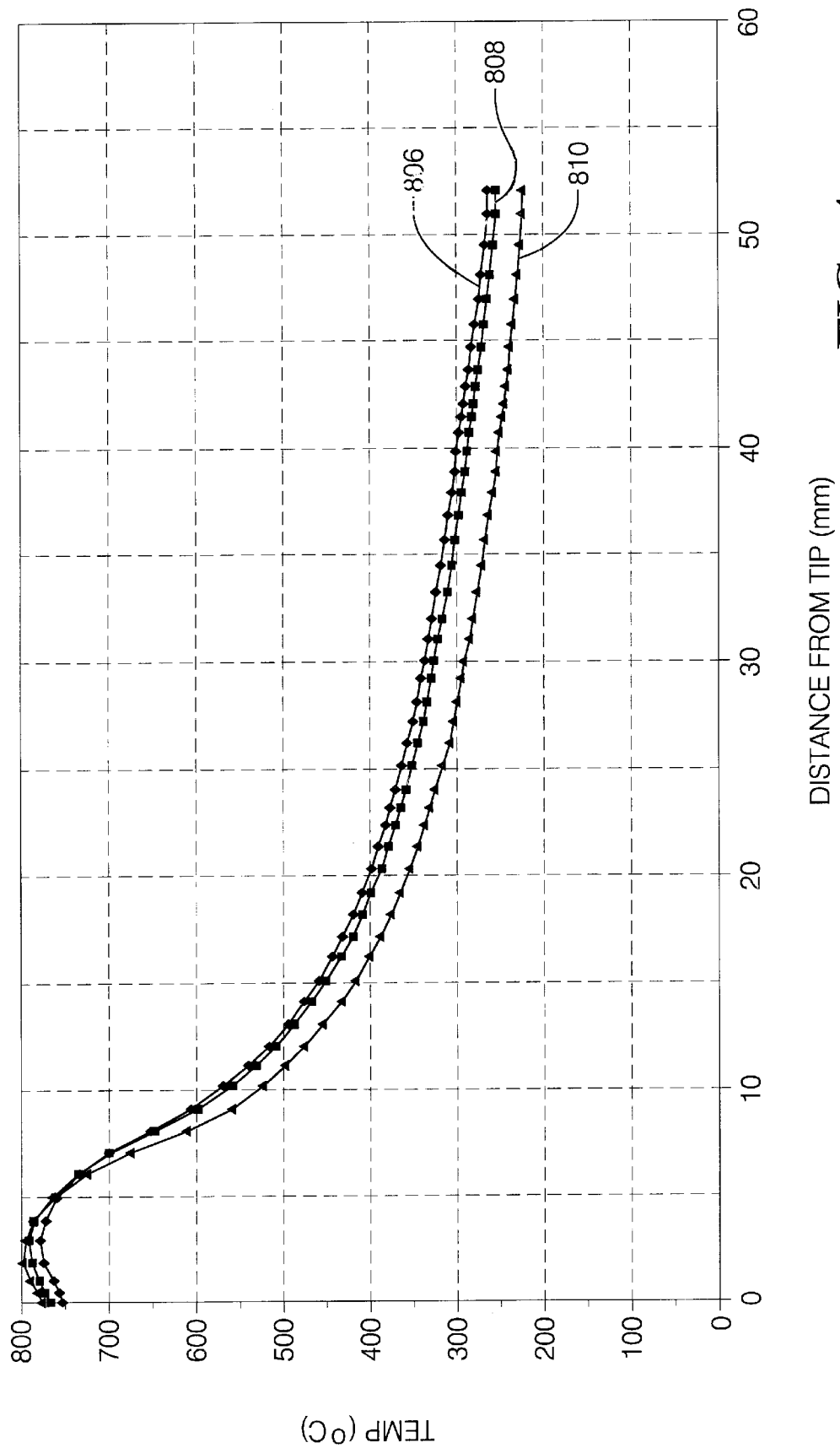
FIG. 4 is a graph showing the temperature along the length of the element of FIG. 2 during operation.

FIG. 4 shows a graph of the steady state temperature along the length of the same three elements shown in FIG. 3. Line 806 represents a conventional sensor with rectangular geometry, line 808 represents a modified geometry sensor with a 5:6 narrow portion 66 width to wide portion 70 width ratio, and line 810 represents a modified geometry sensor with a 2:3 narrow portion 66 width to wide portion 70 width ratio. The graph shows that the temperature of the element along its length is lower for the modified geometry elements than for the rectangular element. The smaller cross-sectional area and volume of the modified geometry elements transfer less heat to the terminal end 59 of the element, which is a desirable result.

Figure 5:
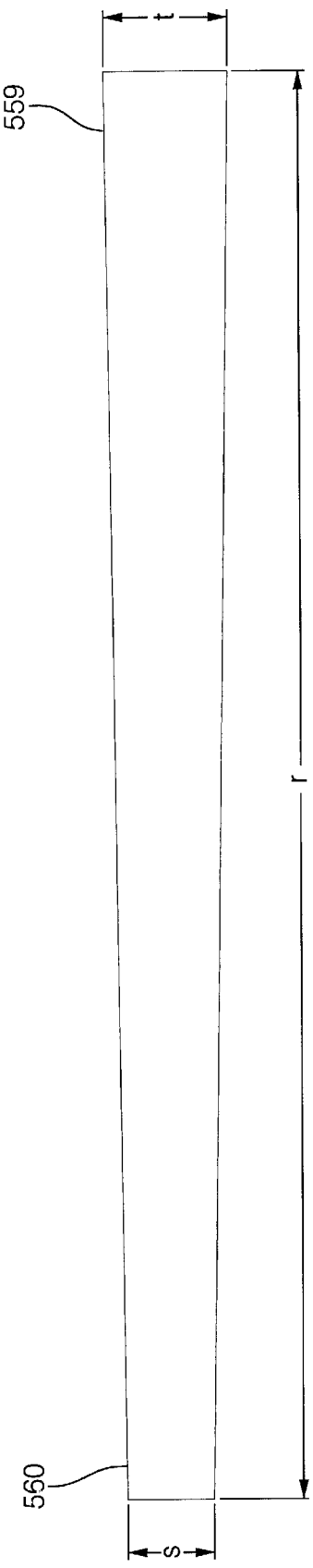
FIG. 5 is a plan view of another embodiment of a layer of a planar exhaust sensor element with a tapered shape.

FIG. 5 illustrates another embodiment of the sensor element, in which the entire length of the sensor element is tapered to form a generally quadrilateral, preferably trapezoidal, element that is generally bilaterally symmetrical about a central axis (dashed line). The ratio of the width of the terminal end 559 "x" of the element to the overall length "r" can be any ratio less than about 1:4, and is preferably about 1:7 to about 1:10, with a ratio of about 1:8 to about 1:9 especially preferred. This shape, beyond the heat transfer benefits described above, provides the benefit of a more secure fit in the finished sensor. The overall tapered shape of the sensor will prevent the element from moving in a direction toward the sensor end 560 if the element should become loosened within the finished sensor.

The trapezoidal taper does not need to begin at the terminal end 659 of the element, however, and, as shown in FIG. 6, it is possible to begin the taper at any point along the length of the element between the sensor end 660 and the terminal end 659. In this embodiment, a generally rectangular terminal portion 75 is disposed adjacent to a generally quadrilateral, preferably trapezoidal tapering portion 77. The proportionate dimensions of the element shown in FIG. 6 are the same as those given for the element shown in FIG. 5. This geometry has a greater area for heater leads, thus allowing for heater leads with lower resistance, which reduces the energy and current required to properly heat the element.

FIG. 7 shows a further embodiment of the sensor element. The element is generally bilaterally symmetrical about a central axis (dashed line), and has a terminal portion 72, a first tapering portion 74, a second tapering portion 76, and a sensor portion 78. The terminal portion 72 is at the terminal end 759 of the element, and has a generally rectangular shape. This portion provides a surface for the attachment of the sensor circuit. The first tapering portion 74 is disposed adjacent to the terminal portion 72, and has a generally quadrilateral, preferably trapezoidal shape. The first tapering portion 74 prevents the element from shifting in the finished sensor as described above. A second tapering portion 76 is disposed adjacent to the first tapering portion 74 opposite the terminal portion 72. The second tapering portion 76 has a generally quadrilateral, preferably trapezoidal shape. A sensor portion 78 is disposed at the sensor end 760 of the element adjacent to the second tapering portion 76 opposite the first tapering portion 74. The terminal portion 72 has a generally rectangular shape.

The first tapering portion 74 has a width "q" on the side that is disposed adjacent to the terminal portion 72. The first tapering portion 74 has a width "p" on the side that is disposed adjacent to the second tapering portion 76. The width "p" which can be any width greater than or equal to the width of the sensor portion 760 "o" and less than the width of the terminal portion 72 "q." The ratio of the length of the sensor portion 78, "n", to the combined length of the first tapering portion 74 and the terminal portion 72 "l"+"k," can be any ratio less than about 1:2, and preferably is about 1:4 to about 1:7, with a ratio of about 2:11 especially preferred. The ratio of the length of the terminal portion 72 "k" to the first tapering portion 74 "l" can be any ratio, with a ratio of about 1:5 to about 1:10 preferred. The ratio of the width of the second tapering portion 76 of the element "m" to the entire length of the element (n+m+l+k) can be any ratio, and preferably is less than about 1:25, with a ratio of about 1:50 especially preferred.

Other embodiments include sensors with element geometries that have non-quadrilateral sensor ends, which can be narrower than the terminal end of the element. These geometries can be, for example, rounded, polygonal, or the like. Any of the above described embodiments can be modified to result in a rounded or polygonal sensor end, with a resulting further reduction in the cross-sectional area of the sensor end of the element. Such a geometry further reduces the required current in the heater circuit, as well as improves the rate at which operating temperature is reached.

The modified geometry of the above described sensor elements reduce the area available at the sensor end of the element, and thereby reduce the area available for the electrolyte, protective layer, and electrodes. The electrolytes and the electrode can be formed in a non-circular shape to provide a greater active sensor area within the reduced space at the sensor end of the element. Any shape that can be formed within the sensor end of the element can be used, with an elongated shape preferred, including, but not limited to, oval, quadrilateral, polygonal, rectangular, and the like, with an oval shape oriented with its major axis aligned with the long axis of the layers preferred.

The sensor is operated by exposing the exhaust gas sensor element to an exhaust gas, and diffusing molecular oxygen in the exhaust gas through said electrochemical cell. The molecular oxygen is ionized at the inner electrode of said electrochemical cell, and the ions are pumped out of the cell. An applied potential between the inner electrode and the outer electrode creates a measurable current, which is proportional to the concentration of oxygen in the exhaust gas. The applied potential is determined by the reference cell circuit output.

The sensor element described above reaches operating temperatures more quickly, for example more than two seconds faster, than conventional sensor elements. Also, since the element provides a taper for a more secure fit of the sensor element in the finished sensor, the sensor element is less likely to shift during routine use. The above described element requires less energy and current than conventional sensors since the volume to be heated at the sensor end of the element is smaller, and reduces the operating temperature of the element at the terminal end.

While preferred embodiments have been shown and described, various modifications and substitutions may be made thereto without departing from the spirit and scope of the invention, including the use of the geometries taught herein in other conventional sensors. Accordingly, it is to be understood that the apparatus and method have been described by way of illustration only, and such illustrations and embodiments as have been disclosed herein are not to be construed as limiting to the claims.

We claim:

1. An exhaust gas sensor element having a length, comprising:
   a plurality of planar layers each having a sensor end and a terminal end opposite the sensor end, wherein the planar layers are disposed in physical contact in a stack, and the sensor end has a width smaller than a terminal end width, the terminal end continuously tapers to the sensor end;
   an electrochemical cell disposed at the sensor end; and
   a plurality of electrode leads disposed in electrical contact with the cell, extending from the cell to the terminal end.

2. The element of claim 1, wherein a ratio of the sensor end width to the terminal end width is about 7:12 to about 11:12, and a ratio of the terminal end width to the element length is about 1:7 to about 1:10.

3. The element of claim 2, wherein the ratio of the sensor end width to the terminal end width is about 2:3 to about 5:6 and the ratio of the terminal end width to the element length is about 1:8 to about 1:9.

4. The element of claim 1, wherein the electrochemical cell further comprises an outer electrode, an inner electrode, and an electrolyte disposed between the outer electrode and the inner electrode.

5. The element of claim 4, wherein the electrolyte has an elongated shape.

6. The element of claim 5, wherein the elongated shape is an oval, rectangle, square, quadrilateral, or polygon.

7. The element of claim 1, wherein each of the layers has an overall trapezoidal geometry.

8. The element of claim 7, wherein a ratio of the sensor end width to the terminal end width is about 7:12 to about 11:12, and a ratio of the terminal end width to the element length is about 1:7 to about 1:10.

9. The element of claim 8, wherein the ratio of the sensor end width to the terminal end width is about 2:3 to about 5:6, and the ratio of the terminal end width to the element length is about 1:8 to about 1:9.

10. An electrochemical cell, comprising:
    a substrate layer with a terminal end and a sensor end, wherein the sensor end is narrower than the terminal end and the terminal end continuously tapers to the sensor end;
    an electrolyte disposed in the sensor end;
    an outer electrode disposed in intimate contact with one side of the electrolyte; and,
    an inner electrode disposed in intimate contact with another side of the electrolyte, opposite the outer electrode.

11. The cell of claim 10, wherein the electrolyte has an elongated shape.

12. The cell of claim 11, wherein the elongated shape is an oval, rectangle, square, quadrilateral, or polygon.

13. A method of sensing oxygen concentration in an exhaust gas comprising:
    exposing an exhaust gas sensor to the exhaust gas, wherein the exhaust gas sensor comprises
      a plurality of layers each having a sensor end and a terminal end opposite the sensor end, wherein the layers are disposed in physical contact in a stack, and the sensor end has a width smaller than a terminal end width, the terminal end continuously tapers to the sensor end;
      an electrochemical cell disposed at the sensor end; and
      a plurality of electrical leads disposed in electrical contact with the cell, extending from the cell to the terminal end;
    diffusing molecular oxygen in the exhaust gas through a gas diffuser to the cell;
    ionizing the molecular oxygen at an inner electrode of the electrochemical cell;
    applying a potential between the inner electrode and an outer electrode of the electrochemical cell; and
    measuring a current produced by the potential.

14. An exhaust gas sensor element having a length, comprising:

a plurality of planar layers each having a sensor end and a terminal portion opposite the sensor end, wherein the planar layers are disposed in physical contact in a stack, and the sensor end has a width smaller than a terminal portion width, wherein the terminal portion continuously tapers to the sensor end an electrochemical cell disposed at the sensor end; and a plurality of electrode leads disposed in electrical contact with the cell, extending from the cell to the terminal end.

15. The element of claim 14, wherein a ratio of the sensor end width to the terminal portion width is about 7:12 to about 11:12, and a ratio of the terminal end width to the element length is about 1:7 to about 1:10.

16. The element of claim 15, wherein the ratio of the sensor end width to the terminal end width is about 2:3 to about 5:6, and the ratio of the terminal end width to the element length about 1:8 to about 1:9.

* * * * *